United States Patent
Hardy et al.

(10) Patent No.: US 7,560,555 B2
(45) Date of Patent: Jul. 14, 2009

(54) PROCESS FOR THE PREPARATION OF PHOSPHITYLATION AGENTS

(75) Inventors: Jonathan Mark Hardy, Mt Pleasant, TN (US); Stephen Edward Dinizo, Mt Pleasant, TN (US)

(73) Assignee: Avecia Biotechnology Inc., Milford, MA (US)

( * ) Notice: Subject to any disclaimer, the term of this patent is extended or adjusted under 35 U.S.C. 154(b) by 256 days.

(21) Appl. No.: 10/539,210

(22) PCT Filed: Dec. 16, 2003

(86) PCT No.: PCT/GB03/05473

§ 371 (c)(1),
(2), (4) Date: Feb. 6, 2006

(87) PCT Pub. No.: WO2004/055030

PCT Pub. Date: Jul. 1, 2004

(65) Prior Publication Data

US 2006/0173187 A1 Aug. 3, 2006

Related U.S. Application Data

(60) Provisional application No. 60/433,788, filed on Dec. 17, 2002.

(51) Int. Cl.
*C07F 9/52* (2006.01)
(52) U.S. Cl. .............................. 546/21; 548/111; 564/12
(58) Field of Classification Search .................. 564/12; 546/21; 548/111
See application file for complete search history.

(56) References Cited

FOREIGN PATENT DOCUMENTS

JP      62-212395    *  9/1987  ................. 564/12
JP      62 212395 A2    9/1987

OTHER PUBLICATIONS

Hamamoto, Shoji et al, "New Approach to the Synthesis of Deoxyribonucleoside Phosphoramidite Derivatives," Chemistry Letters, No. 8, pp. 1401-1404.*
Wilk, A, et al, "The 4-oxopentyl group as a labile phosphate/thiiophosphate protecting group for synthetic oligodeoxyribonucleotides" Tetrahedron Letters, vol. 42 (33), pp. 5635-5639.*
Tawara, Shinichiro et al. "Phosphorodiamidous acid ester derivatives" XP002272471 Databse accession No. 109: 149797 CA.
Hamamoto S. et al.: "New approach to the synthesis of deoxyribonucleoside phosphoramidite derivatives" Chemistry Letters., No. 8, 1986, pp. 1401-1404, XP002272465 JPChemical Society of Japan. Tokyo.
Kruczynski L.J. et al.: "Phenylfluorophosphoranes: axial-equatorial fluorine exchange in RC6H4PF3H and intermolecular exchange in the PhPF2(H) OMe-MeOH-base system" Canadian Journal of Chemistry., vol. 68, No. 3, 1990, pp. 488-491, XP002272466 Canational Research Council. Ottawa.
Heinicke J. et al.: "Synthese von o-Halogenphenoxy-, o-Halogenphenylthio-und o-Halogen-methylanilinoderivaten der IVb-und Vb-Elemente" Journal Fuer Praktische Chemie., vol. 325, No. 3, 1983, pp. 511-516, XP0008028030 DewileyVCH, Weinheim. p. 511, process (A) and p. 514.
Nifant'ev E.E. et al.: "New aspects of the chemistry of pyrrolides of tervalent phosphorus acids" Russian Journal of General Chemistry., vol. 62, No. 7, Dec. 20, 1992, pp. 1201-1208, XP002272467 USConsultants Bureau.
Kibardin A.M. et al.: "Synthesis of ethyl bis (N-butyl-N-isobutenylamido) phosphite and reaction with alpha-chloroacetaldehydes" Bulletin of the Academy of Sciences of the USSR. Division of Chemical Science., vol. 31, No. 3, Sep. 20, 1982, pp. 625-627, XP002272468.
Burgada R.: "Les reactions du carbonyle avec les aminophosphines X. Effect de substitutant dans les reactions d'echange." Bulletin De La Societe Chimique De France., No. 1, 1971, pp. 136-143, XP002272469, Frsociete Francaise De Chime. Paris p. 140, experimental part.
Mitsunobu O. et al.: "Preparation of carboxylic esters and phosphoric esters by the activation of alcohols" Bulletin of the Chemical Society of Japan., vol. 44, No. 12, 1971, pp. 3427-3430, XP002272470 JP Japan Publications Trading Co. Tokyo. p. 3430.
Wilk A et al: "The 4-oxopentyl group as a labile phosphate/thiiophosphate protecting group for synthetic oligodeoxyribonucletides" Tetrahedron Letters, Elsevier Science Publishers, Amsterdam, NL, vol. 42, No. 33, Aug. 13, 2001 pp. 5635-5639, XP004295829.
Nielsen et al., "Thermal Instability of Some Alkyl Phosphorodiamidites", J. Chem. Research, Synop. (1986), pp. 26-27.
Hamamoto et al., "2-(2-Pyridyl)ethyl group: new type protecting group in the synthesis of DNA via phosphoramidite intermediates", Nucleic Acids Research, Symp. Ser. No. 17:93-96, (1986).

* cited by examiner

*Primary Examiner*—Rei-Tsang Shiao
*Assistant Examiner*—Janet L Coppins
(74) *Attorney, Agent, or Firm*—Morgan Lewis & Bockius LLP

(57) ABSTRACT

A process for the preparation of a compound of formula $R^1$—$Y^1$—$P(NR^2R^3)_2$ is provided. The process comprises reacting a compound of formula $PX_3$ with a compound of formula $HNR^2R^3$ to form a compound of formula X—P$(NR^2R^3)_2$; and reacting the compound of formula X—P$(NR^2R^3)_2$ with a compound of formula $R^1$—$Y^1$—H in the presence of a hydrocarbon solvent to form the compound of formula $R^1$—$Y^1$—$P(NR^2R^3)_2$. $R^1$ represents a phosphorus protecting group; $R^2$ and $R^3$ each independently represent an alkyl, prefer-ably a $C_{1-6}$alkyl, group, or $R^2$ and $R^3$ are joined, together with the N to which they are attached, to form a 5-7 membered ring; $Y^1$ represents O or S, preferably O; and X represents a halogen, preferably Cl. The preferred solvent is toluene.

12 Claims, No Drawings

PROCESS FOR THE PREPARATION OF PHOSPHITYLATION AGENTS

This application is a national phase 371 filing based on PCT/GB2003/005473, filed Dec. 16, 2003 and claims priority from U.S. Provisional Application No. 60/433,788, filed Dec. 17, 2002.

The present invention concerns a process for the preparation of phosphitylation agents.

Synthetic oligonucleotides are important diagnostic tools for the detection of genetic and viral diseases. In addition, oligonucleotides and modified oligonucleotides are of interest as therapeutic candidates that inhibit gene expression or protein function. Large scale synthesis of oligonucleotides for use as therapeutic candidates has become increasingly important since FDA approval of an oligonucleotide analog for the treatment of cytomegalovirus (CMV), and several other oligonucleotide analogs are currently in clinical trials. Kilogram quantities of a purified oligonucleotide analog are needed for each clinical trial.

The principal method currently employed for the preparation of oligonucleotide is the phosphoramidite approach. The increasing demand for larger quantities of oligonucleotides has correspondingly increased demand for phosphoramidite compounds. Phosphoramidite compounds are commonly prepared by phosphitylation of a nucleoside with a phosphitylation agent in the presence of an activator. Accordingly, there has been a corresponding increase in demand for phosphitylation agents. Improved or alternative processes for the preparation of phosphitylation agents are therefore needed.

According to the present invention, there is provided a process for the preparation of a compound of formula $R^1$—$Y^1$—$P(NR^2R^3)_2$ which comprises:

a) reacting a compound of formula $PX_3$ with a compound of formula $HNR^2R^3$ to form a compound of formula X—P$(NR^2R^3)_2$; and b) reacting the compound of formula X—$P(NR^2R^3)_2$ with a compound of formula $R^1$—$Y^1$—H in the presence of a solvent to form the compound of formula $R^1$—$Y^1$—$P(NR^2R^3)_2$ wherein $R^1$ represents a phosphorus protecting group;

$R^2$ and $R^3$ each independently represent an alkyl, preferably a Cue alkyl, group, or $R^2$ and $R^3$ are joined, together with the N to which they are attached, to form a 5-7 membered ring;

$Y^1$ represents O or S, preferably O; and

X represents a halogen, preferably Cl; characterised in that the solvent employed in reaction b) is a hydrocarbon solvent.

Phosphorus protecting groups represented by $R^1$ are commonly cleavable phosphorus protecting groups employed in oligonucleotide synthesis, for example substituted or unsubstituted aliphatic groups, such as a methyl group, —$CH_2CH_2$—$Si(CH_3)_2C_6H_5$, —$CH_2CH_2$—$S(O)_2$—$CH_2CH_3$, —$CH_2CH_2$—$C_6H_4$—$NO_2$ and preferably a group of formula —$CH_2CH_2CN$; or substituted or unsubstituted aromatic groups, such as a phenyl or substituted phenyl, for example a 4-chlorophenyl, 2-chlorophenyl, 2-nitrophenyl or 4-nitrophenyl group.

Compounds of formula $R^1$—$Y^1$—H are preferably selected based on the nature of the compound it is desired to produce. An especially preferred compound of formula $R^1$—$Y^1$—H is 2-cyanoethanol.

In the compounds prepared by the process of the present invention, it is preferred that $R^2$ and $R^3$ are the same. It is particularly preferred that both $R^2$ and $R^3$ are —$CH(CH_3)_2$ groups. It is especially preferred that $Y^1$ is O and $R^1$ is —$CH_2CH_2CN$.

Examples of compounds which can be prepared by the process of the present invention include O-β-cyanoethyl-N, N,N',N'-tetraisopropylphosphorodiamidite, (commonly known as "tetraphos"), O-β-cyanoethyl-N,N,N',N'-tetramethylphosphorodiamidite, O-β-cyanoethyl-N,N,N',N'-tetraethylphosphorodiamidite, bis (N,N-diisopropylamino)-2-methyltrifluoroacetylamino-ethoxyphosphine, bis (N,N-diisopropylamino)-2-diphenylmethylsilylethoxyphosphine and O-β-cyanoethyl-bis (N-morpholino) phosphorodiamidite.

Hydrocarbon solvents that can be employed in the process of the present invention include aliphatic and aromatic hydrocarbons. Examples of aliphatic hydrocarbons include pentane, hexane and petroleum ethers. Examples of aromatic hydrocarbons include benzene, toluene, xylene and mesitylene. Toluene is the most preferred solvent.

In many preferred embodiments, reaction a) takes place in the presence of the same solvent as reaction b), and most preferably in the presence of toluene.

The reaction between the compound of formula X—P$(NR^2R^3)_2$ and the compound of formula $R^1$—$Y^1$—H preferably takes place in the presence of a base. Bases which can be employed include inorganic bases, such as sodium carbonate, and organic bases. Organic bases are preferred. Examples of organic bases include aromatic amines such as pyridine, and inorganic amines, such as alkylamines, preferably trialkylamines, such as tri($C_{1-4}$alkyl)amines, and most preferably triethylamine.

The mole ratio of compound of formula $PX_3$ to compound of formula $HNR^2R^3$ in step a) is commonly selected to be in the range of from about 1:1 to about 10:1, and preferably from about 3:1 to about 6:1.

The mole ratio of compound of formula X—$P(NR^2R^3)_2$ to compound of formula $R^1$—$Y^1$—H in step b) is commonly selected to be in the range of from about 1:1 to about 5:1, with mole ratios in the range of from 1:1 to 1.5:1 being especially preferred.

When a base is employed, the mole ratio of base to compound of formula X—$P(NR^2R^3)_2$ is often in the range of from about 0.75:1 to 2:1, and preferably from about 1:1 to 1.3:1.

Step a) of the process according to the present invention is often carried out at a temperature in the range of from ambient temperature, such as from about 15° C. to about 30° C., up to the reflux temperature of the solvent employed, such as from about 50° C. to about 120° C.

Step b) of the process according to the present invention is often carried out at a temperature in the range of from about −25° C. to ambient temperature, such as from about 15° C. to about 30° C., such as from about −20° C. to about 0° C. Temperatures in the range of from −20° C. to −10° C. are especially preferred.

Advantageously, substantially anhydrous reaction conditions are employed.

In many embodiments the process of the present invention is carried out under an inert atmosphere, such as a nitrogen or argon atmosphere.

The product compound of formula $R^1$—$Y^1$—$P(NR^2R^3)_2$ is advantageously separated from the reaction mixture by distillation, and especially preferably by wiped-film distillation.

A particularly preferred embodiment of the present invention comprises a process for the preparation of $\{[(CH_3)_2CH]_2N\}_2$—P—O—$CH_2CH_2CN$, which comprises a) reacting $PCl_3$ with $[(CH_3)_2CH]_2N$—H in toluene to form $\{[(CH_3)_2CH]_2N\}_2$—P—Cl; and b) reacting $\{[(CH_3)_2CH]_2N\}_2$—P—Cl with HO—$CH_2CH_2$CN in toluene to form $\{[(CH_3)_2CH]_2N\}_2$—P—O—$CH_2CH_2CN$.

The present invention is illustrated without limitation by the following Example.

EXAMPLE

Step a)

Diisopropylamine (383 g), toluene (1087 g) and calcium hydride (log) were charged to a nitrogen-flushed, 2 L round-bottom flask equipped with a magnetic stirrer and cold-finger distillation head attached to an $N_2$ bubble and the mixture heated under total reflux (98° C.) for 2 hrs to remove all traces of water. The dried amine/toluene mixture was distilled into an oven-dried nitrogen-flushed, 3 L, 4-neck round-bottom flask equipped with a mechanical stirrer, a 100 mL, pressure-equalizing addition funnel, a thermowell and a condenser attached to an $N_2$ bubbler, and allowed to cool to ambient temperature (ca. 17° C.). Phosphorus trichloride (99.999%, 100 g) was charged from the addition funnel over approximately 30 min. The temperature of the mixture was observed to rise ca. 25° C. The mixture was heated to reflux (100-110° C.) and stirred for 24 hrs; the mixture becoming quite thick with precipitated diisopropylamine hydrochloride. The mixture was cooled to ambient temperature and pressure-filtered under nitrogen to remove the amine salt, all equipment being oven-dried before use. The filter cake was washed with 217 g of toluene, and the combined filtrate and washings distilled in vacuo to remove most of the toluene, the mixture becoming a slush as solids precipitate. When no more toluene distilled, the vacuum was broken with nitrogen and the distillation vessel connected via a cold trap directly to a vacuum pump. Residual toluene was pumped out until the solid product, $\{[(CH_3)_2CH]_2N\}_2$—P—Cl, reached constant weight. This material, 96-97 area-% active by $^{31}P$ NMR was used in Step b) without further purification.

Step b)

Triethylamine (49.4 g), toluene (649.5 g) and calcium hydride (5 g) were charged to a nitrogen-flushed, 1 L round-bottom flask equipped with a magnetic stirrer and cold-finger distillation head attached to an $N_2$ bubbler and the mixture heated under total reflux (98° C.) for 2 hrs to remove all traces of water. The dried mixture was distilled into an oven-dried, nitrogen-flushed, 2 L 3-neck, jacketed round-bottom flask equipped with a mechanical stirrer, a thermowell and a 50 mL pressure-equalizing addition funnel attached to an $N_2$ bubbler and the mixture cooled to below −15° C. using a circulating chiller pumping ethylene glycol/water through the reactor jacket and the product of step (a) (130.3 g) added. Neat 2-cyanoethanol (39.9 g) was added from the addition funnel over approximately 30 min, keeping the temperature below −10° C. The mixture was stirred under nitrogen for 18 hrs at −15 to −18° C. to complete the reaction. The mixture was warmed to ambient temperature and pressure-filtered under nitrogen to remove triethylamine hydrochloride salt, all equipment being oven-dried before use. The toluene was stripped out on a rotary evaporator (bath temperature ca. 50° C.). The vacuum was broken with nitrogen and the distillation vessel connected via a cold trap directly to a vacuum pump and residual toluene removed to yield 139.5 g of crude product. The crude product was distilled through a wiped-film evaporator (heated zone 70° C.; pressure 0.008 mmHg) over 1.5 hrs to afford 115.9 g of product.

If desired, the product can be further purified by flash chromatography, for example using pentane and dry basic alumina, and additional wiped-film distillations.

The invention claimed is:

1. A process for the preparation of a compound of formula $R^1$—$Y^1$—$P(NR^2R^3)_2$ which comprises:
   a) reacting a compound of formula $PX_3$ with a compound of formula $HNR^2R^3$ in the presence of a solvent to form a compound of formula X—$P(NR^2R^3)_2$; and
   b) reacting the compound of formula X—$P(NR^2R^3)_2$ with a compound of formula $R^1$—$Y^1$—H in the presence of a solvent to form the compound of formula $R^1$—$Y^1$—$P(NR^2R^3)_2$; wherein
   $R^1$ represents a methyl group, a group of formula —$CH_2CH_2$—$Si(CH_3)_2C_6H_5$, —$CH_2CH_2$—$S(O)_2$—$CH_2CH_3$ or —$CH_2CH_2$—$C_6H_4$—$NO_2$, a group of formula —$CH_2CH_2CN$, or a phenyl, 4-chlorophenyl, 2-chlorophenyl, 2-nitrophenyl or 4-nitrophenyl group;
   $R^2$ and $R^3$ each independently represent an alkyl group, or $R^2$ and $R^3$ are joined, together with the N to which they are attached, to form a 5-7 membered ring;
   $Y^1$ represents O or S; and
   X represents a halogen;
   characterised in that the solvent is employed in reaction a) and reaction b) and said solvent is a hydrocarbon solvent.

2. A process according to claim 1, wherein $R^1$ represents a group of formula —$CH_2CH_2CN$ and $Y^1$ represents O.

3. A process according to claim 1 or claim 2, wherein $R^2$ and $R^3$ each independently represent a $C_{1-6}$ alkyl group.

4. A process according to claim 3, wherein $R^2$ and $R^3$ represent isopropyl groups.

5. A process according to claim 1, wherein $Y^1$ represents O.

6. A process according to claim 1, wherein X represents Cl.

7. A process according to claim 1, wherein the hydrocarbon solvent is toluene.

8. A process according to claim 1, wherein the reaction between the compound of formula X—$P(NR^2R^3)_2$ and the compound of formula $R^1$—$Y^1$—H in step b) takes place in the presence of a base.

9. A process according to claim 8, wherein the base is a tri($C_{1-4}$ alkyl)amine.

10. A process for the preparation of $\{[(CH_3)_2CH]_2N\}_2$—P—O—$CH_2CH_2CN$, which comprises
   a) reacting $PCl_3$ with $[(CH_3)_2CH]_2N$—H in toluene to form $\{[(CH_3)_2CH]_2N\}_2$—P—Cl; and
   b) reacting $\{[(CH_3)_2CH]_2N\}_2$—P—Cl with HO—$CH_2CH_2CN$ in toluene to form $\{[(CH_3)_2CH]_2N\}_2$—P—O—$CH_2CH_2CN$.

11. A process according to claim 10, wherein substantially anhydrous reaction conditions are employed.

12. A process for the preparation of a compound of formula $R^1$—$Y^1$—$P(NR^2R^3)_2$ which comprises reacting a compound of formula X—$P(NR^2R^3)_2$ with a compound of formula $R^1$—$Y^1$—H in the presence of a solvent to form the compound of formula $R^1$—$Y^1$—$P(NR^2R^3)_2$ wherein
   $R^1$ represents $NCCH_2CH_2$—; $Y^1$ represents O; $R^2$ and $R^3$ are each isopropyl, X is chloro, and the solvent is toluene.

* * * * *

UNITED STATES PATENT AND TRADEMARK OFFICE
CERTIFICATE OF CORRECTION

PATENT NO. : 7,560,555 B2 Page 1 of 1
APPLICATION NO. : 10/539210
DATED : July 14, 2009
INVENTOR(S) : John Mark Hardy and Stephen Edward Dinizo It is certified that error appears in the above-identified patent and that said Letters Patent is hereby corrected as shown below:

In the claims, column 4, claim 1, line 27, before the word "solvent", insert the word --same--.

Signed and Sealed this

Thirteenth Day of April, 2010

David J. Kappos
*Director of the United States Patent and Trademark Office*